United States Patent
Tomoeda et al.

(10) Patent No.: US 12,380,376 B2
(45) Date of Patent: Aug. 5, 2025

(54) SUPPORT SYSTEM AND SUPPORT METHOD

(71) Applicant: Imatec Inc., Matsudo (JP)

(72) Inventors: Atsushi Tomoeda, Tokyo (JP); Takeshi Imazeki, Matsudo (JP); Yasukazu Aoki, Tokyo (JP); Haruhisa Yamamoto, Tokyo (JP); Taku Miyake, Tokyo (JP)

(73) Assignee: SODE-EN CO., LTD., Tokyo (JP)

( * ) Notice: Subject to any disclaimer, the term of this patent is extended or adjusted under 35 U.S.C. 154(b) by 0 days.

(21) Appl. No.: 16/975,243

(22) PCT Filed: Feb. 27, 2019

(86) PCT No.: PCT/JP2019/007553
§ 371 (c)(1),
(2) Date: Aug. 24, 2020

(87) PCT Pub. No.: WO2019/168026
PCT Pub. Date: Sep. 6, 2019

(65) Prior Publication Data
US 2020/0401964 A1    Dec. 24, 2020

(30) Foreign Application Priority Data

Feb. 27, 2018    (JP) .................................. 2018-032748

(51) Int. Cl.
*G06Q 10/0631*    (2023.01)
(52) U.S. Cl.
CPC .............................. *G06Q 10/06311* (2013.01)

(58) Field of Classification Search
None
See application file for complete search history.

(56) References Cited

U.S. PATENT DOCUMENTS

| | | | | |
|---|---|---|---|---|
| 6,404,351 B1 * | 6/2002 | Beinke | ................... | G08G 1/087 340/904 |
| 7,770,847 B1 * | 8/2010 | Severson | ............... | A63H 19/24 246/5 |

(Continued)

FOREIGN PATENT DOCUMENTS

| | | |
|---|---|---|
| CN | 101585464 A | 11/2009 |
| JP | 2002288785 A | 10/2002 |

(Continued)

OTHER PUBLICATIONS

JP 2006-151053 A, Haruki et al., Omron Corp., Jun. 15, 2006, pp. 1-16 (STIC machine translation) (Year: 2006).*

(Continued)

*Primary Examiner* — Darlene Garcia-Guerra
(74) *Attorney, Agent, or Firm* — Tarolli, Sundheim, Covell & Tummino LLP (57) ABSTRACT

A support system according to the present invention is provided with a whereabouts identifying unit configured to identify the position where a person needing care is present, an area identifying unit configured to identify an affected area, in which there is a possibility that the line of movement of the person needing care and the line of movement of an approaching object approaching the person needing care cross each other, and a notification unit configured to output a care request to an output unit existing in the affected area.

6 Claims, 5 Drawing Sheets

(56) References Cited

U.S. PATENT DOCUMENTS

| | | | | |
|---|---|---|---|---|
| 9,434,397 | B2* | 9/2016 | Chung | B61L 3/008 |
| 9,770,382 | B1 | 9/2017 | Ellis | G01S 13/93 |
| 9,781,063 | B2* | 10/2017 | Crawford | H04L 51/046 |
| 9,781,247 | B1* | 10/2017 | Gadepalli | H04W 4/023 |
| 9,905,133 | B1* | 2/2018 | Kumar | G07C 5/0808 |
| 10,037,673 | B1* | 7/2018 | Gray | G08B 21/22 |
| 10,136,295 | B1* | 11/2018 | Chee | H04L 67/125 |
| 10,402,894 | B2* | 9/2019 | Childress | G06Q 30/0281 |
| 10,682,090 | B2* | 6/2020 | Johnson | G01S 13/88 |
| 10,761,542 | B1* | 9/2020 | Fairfield | G05D 1/0027 |
| 11,145,408 | B2* | 10/2021 | Sampath | G16H 40/63 |
| 2001/0010541 | A1* | 8/2001 | Fernandez | G08B 13/19656 |
| | | | | 348/E7.086 |
| 2005/0074141 | A1* | 4/2005 | Tsunashima | G06T 7/254 |
| | | | | 382/218 |
| 2005/0270175 | A1* | 12/2005 | Peddie | G08G 1/096783 |
| | | | | 246/473 R |
| 2008/0170118 | A1* | 7/2008 | Albertson | A61H 3/061 |
| | | | | 348/46 |
| 2008/0304641 | A1* | 12/2008 | Rowe | H04M 11/04 |
| | | | | 345/173 |
| 2009/0009338 | A1* | 1/2009 | Hayashi | G08B 21/0423 |
| | | | | 340/573.1 |
| 2009/0243844 | A1* | 10/2009 | Ishidera | G08B 13/19615 |
| | | | | 382/100 |
| 2010/0144375 | A1* | 6/2010 | Pfister | G07B 15/02 |
| | | | | 455/466 |
| 2011/0140919 | A1* | 6/2011 | Hara | B60Q 1/507 |
| | | | | 340/907 |
| 2011/0276407 | A1* | 11/2011 | Bangera | G06Q 30/02 |
| | | | | 705/14.66 |
| 2011/0276644 | A1* | 11/2011 | Berisford | G08B 21/0476 |
| | | | | 709/206 |
| 2011/0289455 | A1* | 11/2011 | Reville | G06F 3/011 |
| | | | | 715/830 |
| 2012/0154582 | A1* | 6/2012 | Johnson | G06Q 10/00 |
| | | | | 340/521 |
| 2012/0171988 | A1* | 7/2012 | Matsuo | H04L 51/24 |
| | | | | 455/404.2 |
| 2012/0232776 | A1* | 9/2012 | Gontmakher | G06Q 10/047 |
| | | | | 701/117 |
| 2013/0217332 | A1* | 8/2013 | Altman | H04H 60/90 |
| | | | | 455/3.01 |
| 2013/0273938 | A1* | 10/2013 | Ng | G01S 5/06 |
| | | | | 455/456.1 |
| 2013/0293344 | A1* | 11/2013 | Ur | G09B 21/001 |
| | | | | 340/4.1 |
| 2015/0009331 | A1* | 1/2015 | Venkatraman | B61L 27/53 |
| | | | | 348/148 |
| 2015/0035685 | A1* | 2/2015 | Strickland | B60Q 9/008 |
| | | | | 340/901 |
| 2015/0202770 | A1* | 7/2015 | Patron | G06Q 30/0265 |
| | | | | 901/50 |
| 2015/0223731 | A1* | 8/2015 | Sahin | A61B 5/1123 |
| | | | | 600/301 |
| 2015/0269699 | A1* | 9/2015 | Burgess | G06Q 50/14 |
| | | | | 705/325 |
| 2015/0269835 | A1* | 9/2015 | Benoit | H04M 19/04 |
| | | | | 340/539.13 |
| 2016/0345132 | A1* | 11/2016 | Creighton | H04W 4/021 |
| 2017/0132915 | A1* | 5/2017 | Cross | G08G 1/087 |
| 2017/0148241 | A1* | 5/2017 | Kerning | H04W 4/026 |
| 2017/0251347 | A1* | 8/2017 | Mehta | H04W 76/50 |
| 2017/0305440 | A1* | 10/2017 | Oba | B60W 50/082 |
| 2018/0189688 | A1* | 7/2018 | Haidacher | G06Q 10/04 |
| 2018/0235833 | A1* | 8/2018 | Vaillant | G09B 21/003 |
| 2018/0315149 | A1* | 11/2018 | Stona | G06Q 50/30 |
| 2018/0326982 | A1* | 11/2018 | Paris | B60W 30/18154 |
| 2018/0356233 | A1* | 12/2018 | Baqain | H04M 3/4936 |
| 2019/0035104 | A1* | 1/2019 | Cuban | G08B 13/196 |
| 2019/0043340 | A1* | 2/2019 | Kayhani | H04W 4/022 |
| 2019/0188493 | A1* | 6/2019 | Tiziani | G05D 1/0214 |
| 2019/0272748 | A1* | 9/2019 | Cross | G08G 1/056 |
| 2020/0242922 | A1* | 7/2020 | Dulberg | B60W 40/00 |
| 2020/0286384 | A1* | 9/2020 | Borsos | G05D 1/0282 |

FOREIGN PATENT DOCUMENTS

| | | | | |
|---|---|---|---|---|
| JP | 2006151053 | A * | 6/2006 | B61B 1/02 |
| JP | 2010086098 | A | 4/2010 | |
| JP | 2015016704 | A | 1/2015 | |
| JP | 2016081293 | A | 5/2016 | |
| JP | 2016099993 | A * | 5/2016 | G06Q 50/22 |
| JP | 2019016348 | A | 1/2019 | |
| KR | 101481378 | B1 | 1/2015 | |
| KR | 20160096380 | A | 8/2016 | |

OTHER PUBLICATIONS

JP 2016-099993 A, Hidekazu, May 30, 2016, pp. 1-16 (WIPO translate—machine translation) (Year: 2016).*

Chang, Yu-Chun, and Ching-Fu Chen. "Identifying mobility service needs for disabled air passengers." Tourism Management 32.5 (2011): 1214-1217 (Year: 2011).*

Ghazal, Mohammed, et al. "Smart mobile-based emergency management and notification system." 2016 IEEE 4th International Conference on Future Internet of Things and Cloud Workshops (FiCloudW). IEEE, 2016 (Year: 2016).*

Kim, Jee-Eun, et al. "Navigating visually impaired travelers in a large train station using smartphone and Bluetooth low energy." Proceedings of the 31st Annual ACM Symposium on Applied Computing. 2016 (Year: 2016).*

K. Lin, Ting Grace, et al. "Spatial analysis of access to and accessibility surrounding train stations: A case study of accessibility for the elderly in Perth, Western Australia." Journal of Transport Geography 39 (2014): 111-120 (Year: 2014).*

Levasseur, Mélanie, et al. "Importance of proximity to resources, social support, transportation and neighborhood security for mobility and social participation in older adults: results from a scoping study." BMC public health 15 (2015): 1-19 (Year: 2015).*

Huang, Qingfeng, and Ronald Miller. "Reliable wireless traffic signal protocols for smart intersections." ITS America Annual Meeting. 2004 (Year: 2004).*

Cortellazzi, Jacopo, et al. "Crowdsensing and proximity services for impaired mobility." 2016 IEEE Symposium on Computers and Communication (ISCC). IEEE, 2016 (Year: 2016).*

Carmien, Stefan, et al. "Socio-technical environments supporting people with cognitive disabilities using public transportation." ACM Transactions on Computer-Human Interaction (TOCHI) 12.2 (2005): 233-262 (Year: 2005).*

Soltani, Seyed Hassan Khalifeh, et al. "Accessibility for disabled in public transportation terminal." Procedia-Social and Behavioral Sciences 35 (2012): 89-96 (Year: 2012).*

Marco, Alvaro, et al. "Location-based services for elderly and disabled people." Computer communications 31.6 (2008): 1055-1066 (Year: 2008).*

Chinese Office Action for CN application No. 201980014758.1, dated Apr. 25, 2025, (machine translation) (Year: 2025).*

JP2018-032748. Refusal Notice (machine translation) (Year: 2022).*

European Search Report for corresponding European Patent Application No. 19 76 0105 dated Oct. 18, 2021.

European Office Action for EP application No. 19 760 105.7, dated Jul. 24, 2024, 10 pages.

Korean Office Action for KR application No. 10-2020-7027115, dated Jan. 17, 2025, 17 pages.

EESR for EP application No. 19760105.7, dated Oct. 27, 2021, 12 pages.

Chinese Office Action for CN application No. 201980014758.1, dated Apr. 25, 2025, 12 pages.

* cited by examiner

Fig.9

SUPPORT SYSTEM AND SUPPORT METHOD

RELATED APPLICATIONS

The present invention is a U.S. National Stage under 35 USC 371 patent application, claiming priority to Serial No. PCT/JP2019/007553, filed on 27 Feb. 2019; which claims priority of JP 2018/032748, filed on 27 Feb. 2018, the entirety of both of which are incorporated herein by reference.

TECHNICAL FIELD

The present disclosure relates to an assistance system and an assistance method for a user that requires attention or assistance.

BACKGROUND ART

There have been techniques for assisting persons requiring attention such as handicapped persons (refer to, for example, Patent Documents 1 and 2). With the technique described in Patent Document 1, a communication terminal requests for route information including train station information, displays the route information, and transmits destination station information selected from the train station information. A management terminal installed in a train transmits the route information and transmits generated destination information. A management terminal installed in a station displays the destination information and transmits reception information to the communication terminal.

With the technique described in Patent Document 2, a device installed at an entrance of a public vehicle, such as a train or a bus, or a waiting area detects or reads a non-contact IC media and issues a notification about a socially vulnerable person carrying the non-contact IC media to other passengers inside or outside the vehicle and an operation manager through wired or wireless communication.

PRIOR ART DOCUMENTS

Patent Documents

Patent Document 1: Japanese Laid-Open Patent Publication No. 2010-86098
Patent Document 2: Japanese Laid-Open Patent Publication No. 2016-99993

SUMMARY OF THE INVENTION

Problems that the Invention is to Solve

The techniques described in Patent Documents 1 and 2 issue a notification about the state of a person requiring attention. However, the attention-requiring person still needs to perform a predetermined operation such as selecting a destination station or having the non-contact media read. Such an operation can be a burden for the attention-requiring person and the person will not be efficiently assisted. Appropriate attention and assistance cannot be provided unless information of an attention-requiring person is output at an appropriate location corresponding to where such a person is located.

Means for Solving the Problems

According to one embodiment of the present disclosure, an assistance system includes a location determining unit configured to determine a location of an attention-requiring person, an area determining unit configured to determine an affected area where a flow line of the attention-requiring person will potentially intersect with a flow line of a nearby object approaching the attention-requiring person, and a notification unit configured to output an attention request to an output unit that is present in the affected area.

According to one embodiment of the present disclosure, a method for assisting cooperation for a user that requires attention using an assistance system that includes a location determining unit, an area determining unit, and a notification unit is provided. The method includes determining a location of an attention-requiring person with the location determining unit, determining an affected area where a flow line of the attention-requiring person will potentially intersect with a flow line of a nearby object approaching the attention-requiring person with the area determining unit, and outputting an attention request to an output unit that is present in the affected area with the notification unit.

According to one embodiment of the present disclosure, an assistance system includes circuitry. The circuitry is configured to execute determining a location of an attention-requiring person, determining an affected area where a flow line of the attention-requiring person will potentially intersect with a flow line of a nearby object approaching the attention-requiring person, and outputting an attention request to an output unit that is present in the affected area.

MODES FOR CARRYING OUT THE INVENTION

An assistance system and an assistance method according to one embodiment will now be described with reference to FIGS. 1 to 5.

Figure 1:
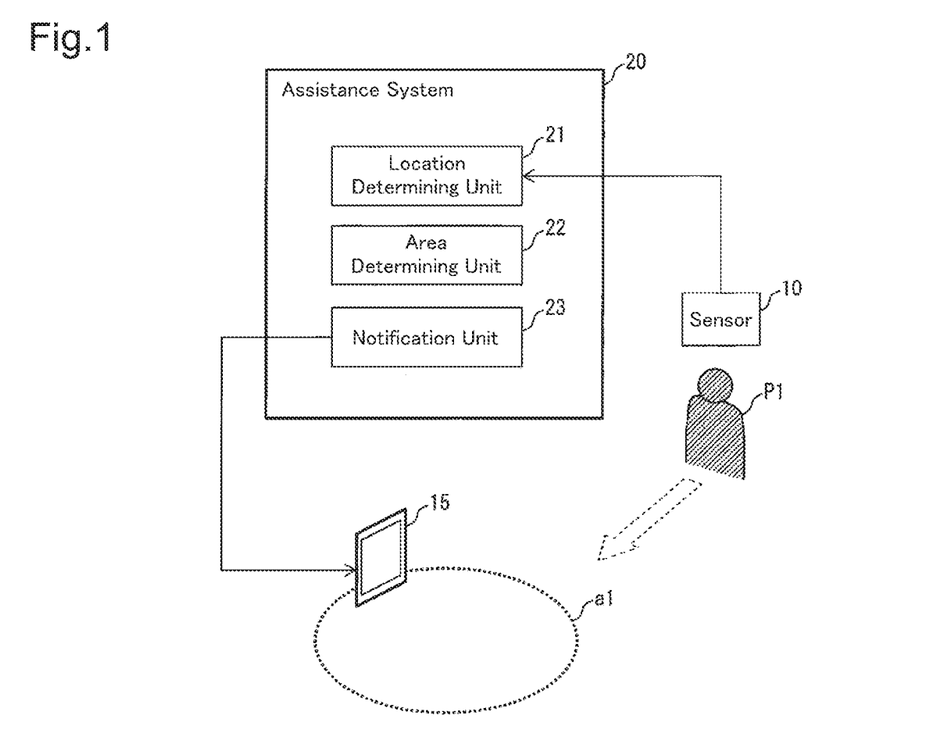
FIG. 1 is a schematic diagram of a system according to one embodiment.

As shown in FIG. 1, in the present embodiment, an assistance system 20 assists an attention-requiring person (user) P1. The attention-requiring person P1 may include, but is not limited to, a person requiring assistance such as a physically impaired person due to disability, senility, injury, or the like, a pregnant woman, a person with a baby stroller, a person with an infant, and a socially or environmentally vulnerable person such as a foreigner. The assistance system 20 transmits an attention request for the attention-requiring person P1 to a nearby object. Such a nearby object will now be described. (1) The nearby object may be staying in place. The nearby object may include, for example, an object that approaches an attention-requiring person as the attention-requiring person or a movable body that the attention-requiring person is riding moves. (2) The attention-requiring person may be staying in place. The nearby object may include an object that approaches the attention-requiring person by moving toward the person. (3) The nearby object may include an object that approaches the attention-requiring person as the attention-requiring person and the nearby object both move.

The assistance system 20 includes a computer that distributes an attention request based on the location of the attention-requiring person P1. In the present embodiment, the assistance system 20 is implemented by, for example, a server computer. However, the assistance system 20 may have any hardware structure. Part or all of the assistance system 20 may be implemented by a mobile terminal carried by the attention-requiring person P1, output means of an attention request, a mobile terminal or output device connected to notification means, or the like. The assistance system 20 is connected to a sensor 10 and an output unit 15 by a network.

The sensor 10 detects the location of the attention-requiring person P1. The sensor 10 is, for example, a monitoring camera installed in a facility such as a train station. In this case, an image captured by the monitoring camera is used to determine the presence or the location of the attention-requiring person P1. The presence or the location of the attention-requiring person P1 may be determined using position information that is obtained by detecting the global positioning system (GPS) of a mobile terminal carried by the attention-requiring person P1, a beacon, or terrestrial magnetism. That is, the presence and the location of the attention-requiring person P1 may be determined based on position information obtained by the mobile terminal.

The output unit 15 outputs various types of messages. The output unit 15 may include a mobile terminal carried by a person near the attention-requiring person P1. The output unit 15 may be installed in a facility and include a display or the like that shows various types of information. The output unit 15 issues a notification about obtained information using light, text display, vibration, sound, or the like.

The assistance system 20 includes a location determining unit 21, an area determining unit 22, and a notification unit 23. The location determining unit 21, the area determining unit 22, and the notification unit 23 may be circuitry including 1) one or more processors that run on a computer program (software), 2) one or more dedicated hardware circuits such as application-specific integrated circuits (ASIC) that execute at least part of various processes, or 3) a combination thereof. The processor includes a CPU and memories such as a RAM and a ROM. The memories store program codes or commands configured to cause the CPU to execute processes. The memories, or computer-readable media, include any type of media that is accessible by general-purpose computers and dedicated computers.

The location determining unit 21 executes a process that determines the location of the attention-requiring person P1. The determination of the location uses information obtained by the sensor 10.

The area determining unit 22 executes a process that determines an affected area a1 based on the location and the movement state of the attention-requiring person P1. The affected area a1 is a region where the flow line of the attention-requiring person P1 will potentially intersect with the flow line of a nearby object such as a person or a vehicle. A moving nearby object may approach the attention-requiring person P1 who is staying in place. Alternatively, the moving attention-requiring person P1 may approach a nearby object that is staying in place. As described above, the attention-requiring person P1 and a nearby object may both move and approach each other. Further, the attention-requiring person P1 may move itself or a movable body that the attention-requiring person P1 is riding may move. The area determining unit 22 determines the affected area a1 by obtaining the flow line of the attention-requiring person P1 and/or a region that may include the flow line of a nearby object.

The location and the movement state of a nearby object may be determined using the sensor 10 described above. In this case, position information may be obtained from an image captured by a monitoring camera installed in a facility, a location detection device such as a beacon device, or a mobile terminal carried by a person near the attention-requiring person P1. The location and the movement state of a movable body (transportation such as train or bus) moving based on a set schedule may be determined based on a schedule as described below.

The notification unit 23 executes a process that finds an output unit 15 that is present in the affected area a1 and outputs information about the attention-requiring person P1 to the output unit 15. The assistance system 20 includes an information storage unit that records output unit information for finding an output unit 15 in each area. The information storage unit may record information related to displays or loudspeakers arranged in predetermined areas and mobile terminals that are present in the predetermined areas.

Processing Procedure Executed by Assistance System 20

Figure 2:
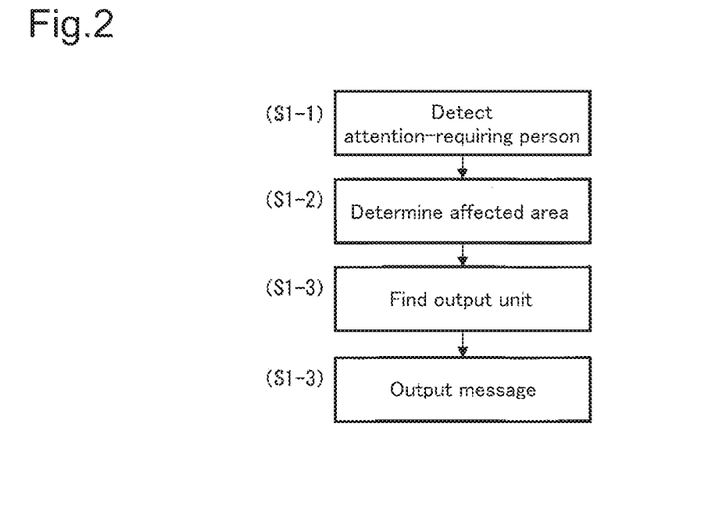
FIG. 2 is a diagram showing a processing procedure according to the embodiment.

A processing procedure executed by the assistance system 20 will now be summarized with reference to FIG. 2.

The location determining unit 21 of the assistance system 20 executes a process for detecting an attention-requiring person (step S1-1). Specifically, the location determining unit 21 uses the sensor 10 and determines the location and the movement state of the attention-requiring person P1.

The area determining unit 22 of the assistance system 20 executes a process for determining an affected area (step S1-2). Specifically, the area determining unit 22 predicts the flow line of the attention-requiring person P1 based on the determined location and movement state (such as movement direction) of the attention-requiring person P1. The area determining unit 22 determines that a region having a reference width for the flow line is the affected area a1.

The notification unit 23 of the assistance system 20 executes a process for finding an output unit associated with the affected area (step S1-3). Specifically, the notification unit 23 uses the output unit information to find an output unit 15 in the affected area a1. The notification unit 23 also uses the sensor 10 to find an output unit 15 in the affected area a1 that the attention-requiring person P is approaching or the affected area a1 that the attention-requiring person P may approach in the future.

The notification unit 23 of the assistance system 20 executes a process for outputting a message (step S1-4). Specifically, the notification unit 23 transmits an attention request for the attention-requiring person P1 to the found output unit 15.

Figure 4:
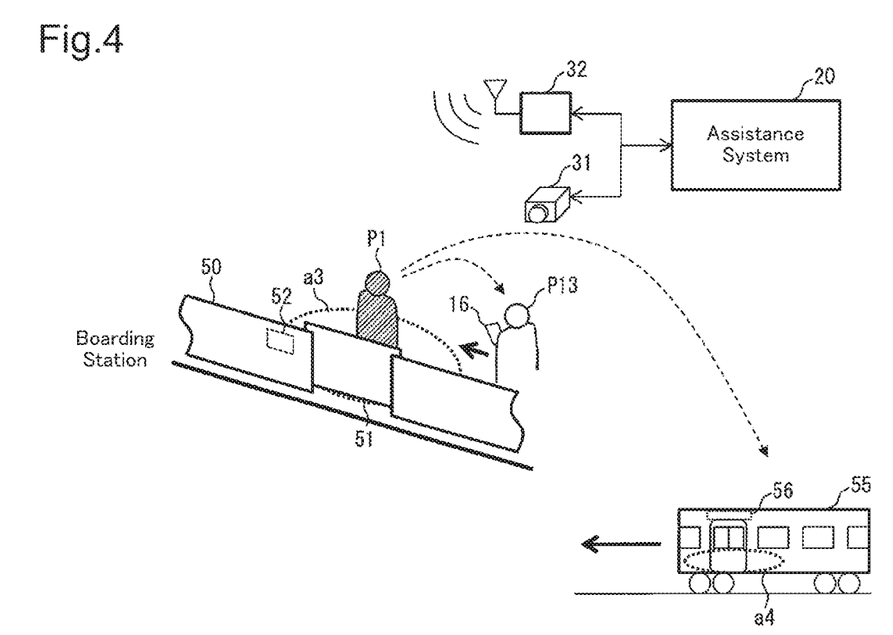
FIG. 4 is a diagram illustrating an assist process executed when an attention-requiring person is waiting on a platform according to one example.
Figure 5:
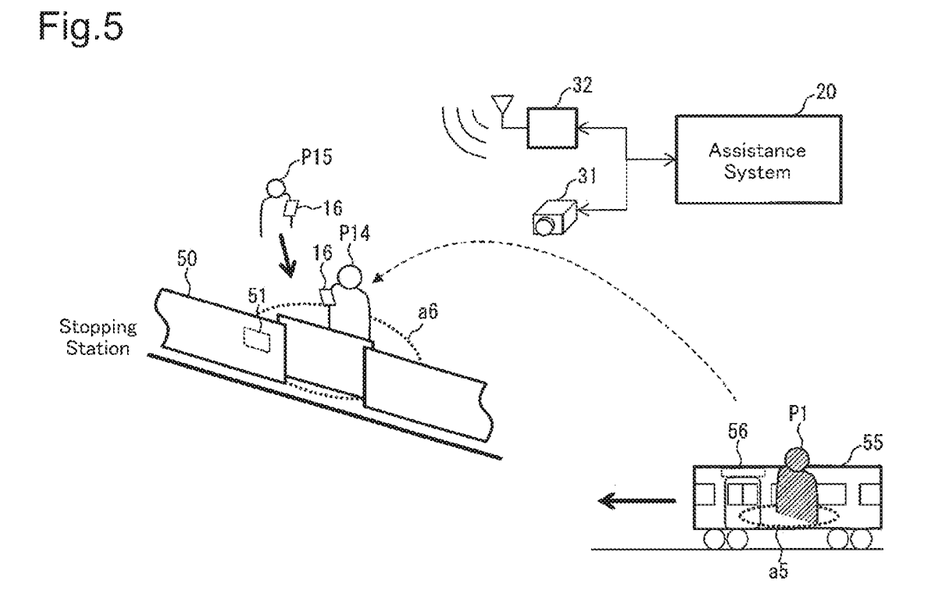
FIG. 5 is a diagram illustrating an assist process executed when an attention-requiring person is traveling by train according to one example.

Processing Procedure Executed when Attention-Requiring Person P1 Uses Railroad According to One Example A processing procedure executed when the attention-requiring person P1 uses a railroad (public transportation) according to one example will now be described with reference to FIGS. 3 to 5. In this case, it is assumed that the attention-requiring person P1 will board a train at a station.

Figure 3:
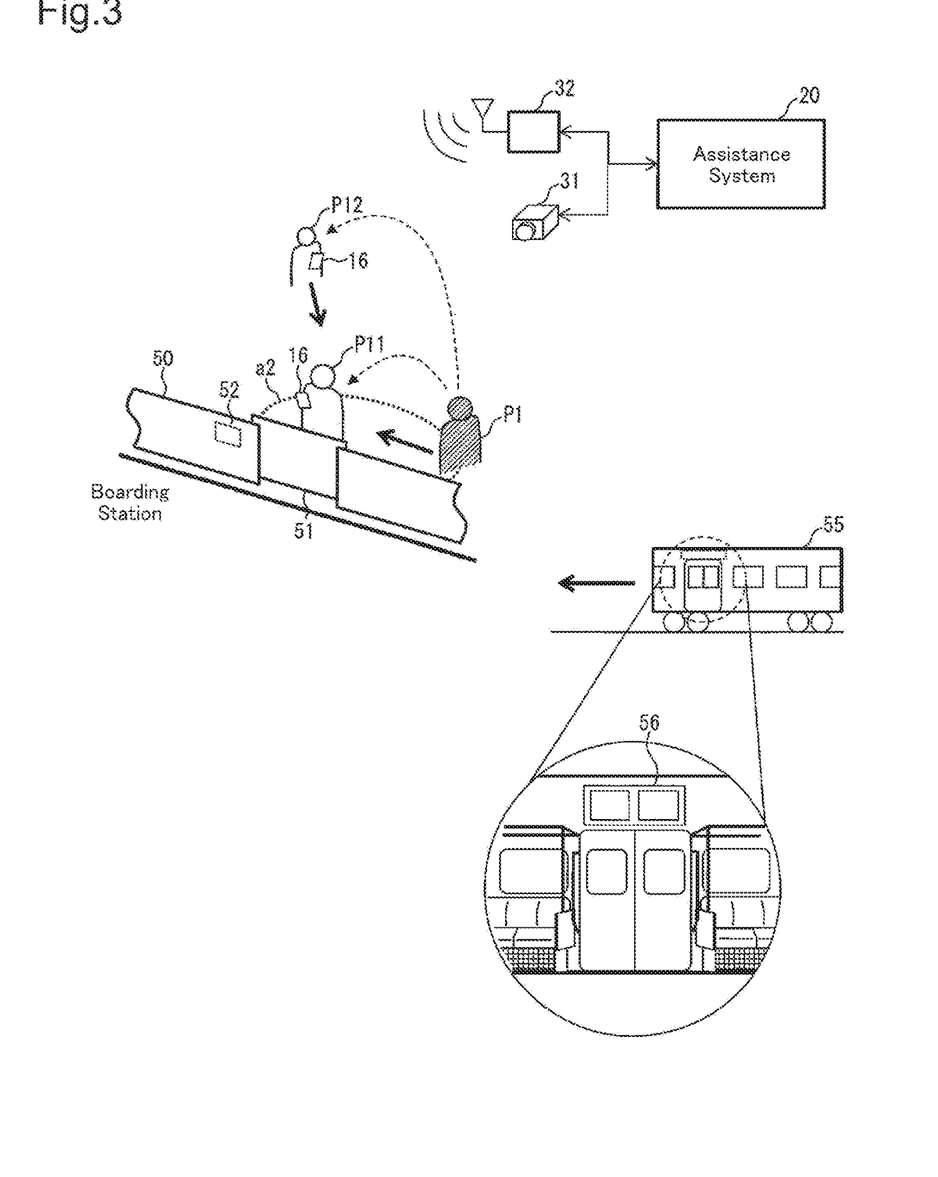
FIG. 3 is a diagram illustrating an assist process executed when an attention-requiring person moves in a train station according to one example.

As shown in FIG. 3, the sensor 10 may be a monitoring camera 31 installed in the train station. A platform in the station includes a platform fence 50. The platform fence 50 includes a display 52 that outputs a message in the proximity of a platform door 51. In this case, the information storage unit of the assistance system 20 stores station map information including the image-captured region of the monitoring camera 31 and the location where the platform door 51 is installed. The information storage unit also stores a train operation schedule. Trains arriving at the station can be found from the operation schedule.

A train 55 includes a display 56 that outputs various types of information in the proximity of each train door.

It is assumed that passengers at the station are carrying mobile terminals 16. A person of which the distance to the attention-requiring person P1 is decreasing will be referred to as a nearby person.

The train station includes a communication device 32. The communication device 32 transmits a message to a mobile terminal 16 in a predetermined area or to a specific mobile terminal 16. Communication may be performed using beacon technology that allows for communication with a peer-to-peer network.

In the present embodiment, the mobile terminal 16, the display 52, and the display 56 correspond to the output unit 15.

Assist Process Executed when Attention-Requiring Person P1 Moves in Train Station An assist process executed when the attention-requiring person P1 moves in the train station will now be described with reference to FIGS. 2 and 3.

As shown in FIG. 2, the location determining unit 21 of the assistance system 20 executes the process for detecting the attention-requiring person (step S1-1). Specifically, the location determining unit 21 obtains a captured image from the monitoring camera 31. The location determining unit 21 determines the location and the movement state of the attention-requiring person P1 through image recognition of the captured image.

The area determining unit 22 of the assistance system 20 executes the process for determining an affected area (step S1-2). Specifically, the area determining unit 22 uses the captured image to predict a flow line based on the location and the movement direction of the attention-requiring person P1. The area determining unit 22 determines the affected area a2 based on the predicted flow line. If the area determining unit 22 determines that the attention-requiring person P1 is moving toward the platform door 51 installed in the platform, the area determining unit 22 determines that the affected area a2 is a region extending to the platform door 51.

The notification unit 23 of the assistance system 20 executes the process for finding an output unit associated with the affected area (step S1-3). Specifically, the notification unit 23 finds an output unit 15 associated with the affected area a1. For example, the notification unit 23 uses the station map information and finds the display 52 installed in the proximity of the platform door 51 in the affected area a1. The notification unit 23 further finds an output unit 15 that is a mobile terminal 16 of a nearby person P11 in the proximity of the platform door 51. The notification unit 23 further finds an output unit 15 that is a mobile terminal 16 of a nearby person P12 approaching the affected area a1. Specifically, the notification unit 23 finds the mobile terminal 16 of the nearby person P12 who may enter the affected area a1 based on the movement speed of the nearby person P12.

The notification unit 23 of the assistance system 20 executes the process for outputting a message (step S1-4). Specifically, the notification unit 23 transmits an attention request for the attention-requiring person P1 to the found output units 15 (that is, display 52 and mobile terminals 16).

Assist Process Executed when Attention-Requiring Person P1 is Waiting on Platform An assist process executed when the attention-requiring person P1 is waiting on a platform will now be described with reference to FIG. 4.

The location determining unit 21 of the assistance system 20 executes the process for detecting the attention-requiring person (step S1-1). Specifically, the location determining unit 21 determines the location and the movement state (waiting) of the attention-requiring person P1 through image recognition of a captured image of the monitoring camera 31.

The area determining unit 22 of the assistance system 20 executes the process for determining an affected area (step S1-2). Specifically, the area determining unit 22 uses the captured image and determines an affected area a3 based on the location of the waiting attention-requiring person P1. The area determining unit 22 determines that the affected area a3 is the vicinity of the platform door 51 where the attention-requiring person P1 is waiting. The area determining unit 22 uses the operation schedule stored in the information storage unit and finds a train 55 that will arrive at the train station. The area determining unit 22 determines that an affected area a4 is the vicinity of a train door of the train 55 that is corresponding to the platform door 51 where the attention-requiring person P1 is waiting near.

The notification unit 23 of the assistance system 20 executes the process for finding an output unit associated with an affected area (step S1-3). Specifically, the notification unit 23 finds an output unit 15 associated with the affected areas a3, a4. For example, the notification unit 23 uses a captured image of the monitoring camera 31 and the communication device 32 to find a nearby person P13 approaching the affected area a3 and determines that a mobile terminal 16 of the nearby person P13 is the output unit 15. The notification unit 23 further determines that the display 56 in the affected area a4 located in the vicinity of the train door is the output unit 15.

The notification unit 23 of the assistance system 20 executes the process for outputting a message (step S1-4). Specifically, the notification unit 23 transmits an attention request for the attention-requiring person P1 to the found output units 15 (that is, mobile terminal 16 and display 56).

Assist Process Executed when Attention-Requiring Person P1 is Traveling by Train An assist process executed when the attention-requiring person P1, who was waiting on a platform, boards a train and travels will now be described with reference to FIG. 5.

The location determining unit 21 of the assistance system 20 executes the process for detecting the attention-requiring person (step S1-1). Specifically, the location determining unit 21 determines the location of a train door of the train that the attention-requiring person P1 has boarded from the image recognition of a captured image of the monitoring camera 31 of the station. The determination of the location of the train door may use a beacon device installed in the train door to detect a mobile terminal carried by the attention-requiring person P1. The location of the attention-requiring person P1 moves as the train travels.

The area determining unit 22 of the assistance system 20 executes the process for determining an affected area (step S1-2). Specifically, the area determining unit 22 determines that the vicinity of the train door of the train that the attention-requiring person P1 has boarded is an affected area a5. The area determining unit 22 uses the operation schedule stored in the information storage unit to find the next station for the train that the attention-requiring person P1 has boarded. The area determining unit 22 determines that the vicinity of a platform door 51 of the determined station corresponding to the location of the train door of the train that the attention-requiring person P1 has boarded is an affected area a6.

The notification unit 23 of the assistance system 20 executes the process for finding an output unit associated with an affected area (step S1-3). Specifically, the notification unit 23 finds an output unit 15 that is the display 56 in the affected area a5 located in the vicinity of the train door. The notification unit 23 also finds an output unit 15 that is the display 52 installed in the affected area a6 in the vicinity of the platform door 51 at the next station.

The notification unit 23 further detects a mobile terminal 16 carried by a person in the vicinity of the affected area a6 with the communication device 32 to find an output unit 15.

The notification unit 23 uses a captured image of the monitoring camera 31 and the communication device 32 so that the notification unit 23 finds a nearby person P14 in the affected area a6 and a nearby person P15 approaching the affected area a6 and also determines that a mobile terminal 16 of the nearby person P15 is an output unit 15.

The notification unit 23 of the assistance system 20 executes the process for outputting a message (step S1-4). Specifically, the notification unit 23 transmits an attention request for the attention-requiring person P1 to the found output units 15 (that is, displays 52, 56 and mobile terminals 16).

The present embodiment has the following advantages.

(1) The assistance system 20 executes the process for detecting an attention-requiring person (step S1-1) and the process for determining an affected area (step S1-2). This determines the region where attention and assistance are necessary in accordance with the location and the movement state of the attention-requiring person.

(2) The assistance system 20 executes the process for finding an output unit associated with an affected area (step S1-3) and the process for outputting a message (step S1-4). This outputs a message in a region where attention and assistance are necessary for the attention-requiring person P1.

(3) A message is output to the mobile terminal 16 of a person that is in an affected area and the mobile terminals 16 of nearby persons P11, P12, P13, P15 who are approaching the affected area. This issues an attention request to those carrying the mobile terminals 16.

(4) A message is output to the display 52 in a train station. This issues an attention request to persons that are not carrying a mobile terminal.

(5) In the assistance process, which is executed when the attention-requiring person P1 is waiting on a platform, the operation schedule is used to find a train approaching the train station where the attention-requiring person P1 is in to output a message on the display 56 of the train. This issues an attention request for the attention-requiring person P1 located in the station to passengers of the train.

(6) The assistance process, which is executed when the attention-requiring person P1 is traveling by train, uses the operation schedule to determine a train station for the train that the attention-requiring person P1 has boarded and outputs a message on the display 52 located in the vicinity of the attention-requiring person P1 when the train arrives at the station. This issues an attention request for the attention-requiring person P1, who is on the train, to persons waiting for the train in the station.

The present embodiment may be modified as described below. The present embodiment and the following modifications can be combined as long as the combined modifications are not in contradiction.

The above embodiment is described with an example in which the assist process is executed when the attention-requiring person P1 uses the train, which is a movable body. The assist process may also be executed when the attention-requiring person P1 is not using a train. For example, the movable body may be an elevator or the like in a building.

A movable body including an elevator in accordance with one example will now be described with reference to FIGS. 6 to 8.

Figure 6:
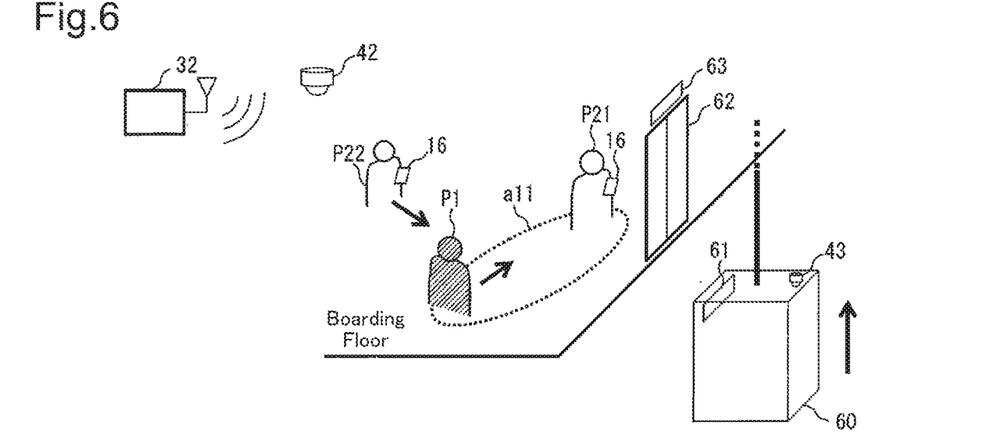
FIG. 6 is a diagram illustrating an assist process executed when an attention-requiring person is moving on a floor to board an elevator in accordance with another example.

FIG. 6 illustrates a case when assisting the attention-requiring person P1 who is on a floor where he or she will board the elevator. The floors of the building each include a monitoring camera 42. The elevator includes a cage 60 with a monitoring camera 43. The building includes the communication device 32 that is used to find the attention-requiring person P1 and a nearby person and output a message to the mobile terminal 16. The cage 60 of the elevator includes a display 61 in the vicinity of its door. The floor at which the elevator stops includes a display 63 in the vicinity of an elevator door 62.

If the attention-requiring person P1 is moving on the floor where he or she will board the elevator, the location determining unit 21 of the assistance system 20 will detect the attention-requiring person P1 with the monitoring camera 42 on the floor.

The area determining unit 22 of the assistance system 20 determines the flow line of the attention-requiring person P1 from a captured image of the monitoring camera 42 and determines an affected area a11 based on the flow line.

The notification unit 23 of the assistance system 20 finds that a mobile terminal 16 of a nearby person P21 inside the determined affected area a11 and a mobile terminal 16 of a nearby person P22 approaching the determined affected area a11 are output units 15.

The notification unit 23 transmits an attention request for the attention-requiring person P1 to the found output units 15.

Figure 7:
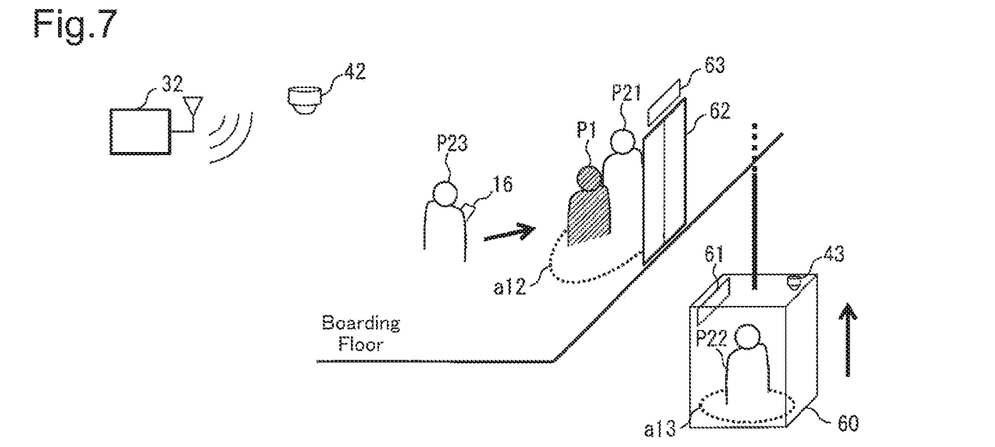
FIG. 7 is a diagram illustrating an assist process executed when an attention-requiring person is waiting for an elevator in accordance with another example.

FIG. 7 illustrates a case in which the attention-requiring person P1 is waiting for an elevator in front of an elevator door 62.

The location determining unit 21 of the assistance system 20 detects the attention-requiring person P1 using the monitoring camera 42 on the floor, and the area determining unit 22 determines an affected area a12 located in the vicinity of the elevator door 62. The area determining unit 22 further communicates with a controller of the elevator to obtain information of the cage 60 that will stop at the floor and determines that the inner space of the cage 60 is an affected area a13.

The notification unit 23 of the assistance system 20 finds that a mobile terminal 16 of a nearby person P21 inside the determined affected area a12 and a mobile terminal 16 of a nearby person P23 approaching the determined affected area a12 are output units 15. The notification unit 23 further determines that a mobile terminal 16 of a nearby person P24 inside the affected area a13 of the cage 60, which will stop at the boarding floor, is an output unit 15.

The notification unit 23 of the assistance system 20 transmits an attention request for the attention-requiring person P1 to the found output units 15.

Figure 8:
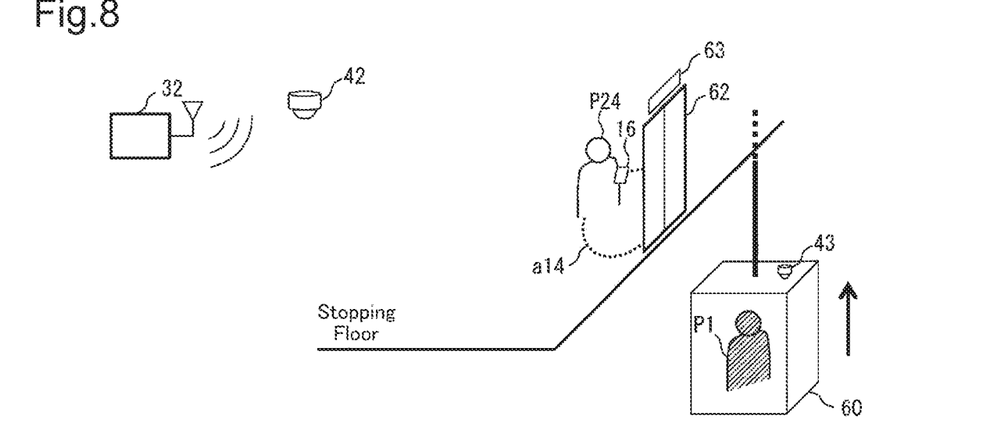
FIG. 8 is a diagram illustrating an assist process executed when an attention-requiring person is moving on an elevator in accordance with another example.

FIG. 8 illustrates a case in which the attention-requiring person P1 is in the cage 60 of the elevator.

The location determining unit 21 of the assistance system 20 uses the monitoring camera 42 in the cage 60 and detects the attention-requiring person P1.

The area determining unit 22 of the assistance system 20 communicates with a management system of the elevator to obtain information on the floor where the cage 60 will stop next. The area determining unit 22 determines that the vicinity of the elevator door 62 on the stopping floor is an affected area a14.

The notification unit 23 of the assistance system 20 finds that the display 63 in the vicinity of the affected area a14 is an output unit 15. The notification unit 23 may find that the mobile terminal 16 of a nearby person P25 in the affected area a14 is an output unit 15.

The notification unit 23 of the assistance system 20 transmits an attention request for the attention-requiring person P1 to the found output units 15.

In the above embodiment, examples of the assist processes executed to assist the attention-requiring person P1 in a transportation facility have been described. Assist processes are not limited to assistance for the attention-requiring person P1 in such facilities. Assist processes may be executed to assist the attention-requiring person P1, for example, outside a facility.

Figure 9:
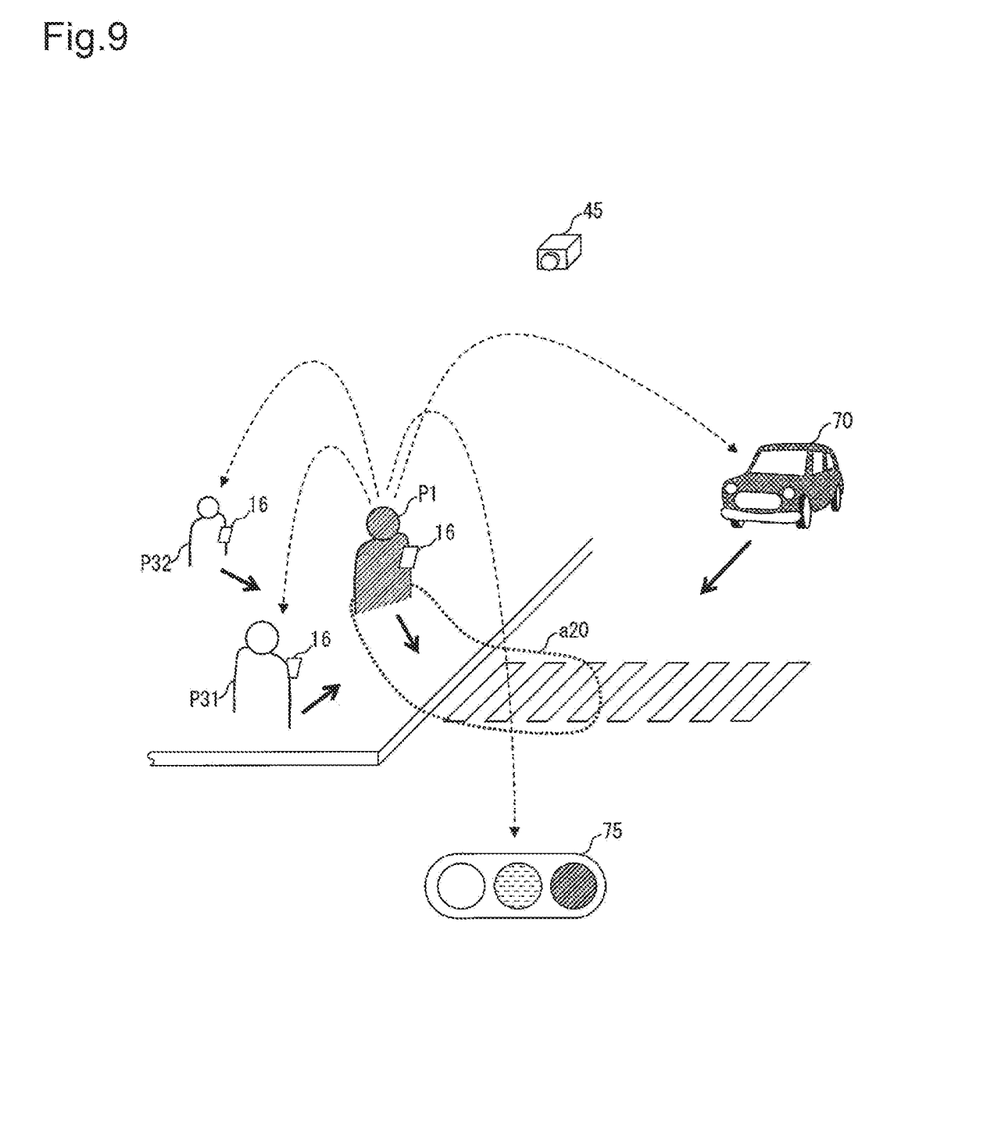
FIG. 9 is a diagram illustrating an assist process executed to assist an attention-requiring person on a street in accordance with another example.

FIG. 9 illustrates a case when assisting the attention-requiring person P1 on a street. The location determining unit 21 of the assistance system 20 uses a monitoring camera installed on a street and a mobile terminal of the attention-requiring person P1 to find where the attention-requiring person P1 is located.

The area determining unit 22 of the assistance system 20 determines an affected area a20 based on the flow line of the attention-requiring person P1.

The notification unit 23 of the assistance system 20 finds mobile terminals 16 of nearby persons P31, P32 having flow lines that will potentially overlap or intersect with the affected area a20.

The notification unit 23 further finds a vehicle 70 of which flow line will potentially overlap or intersect with the affected area a20 from the traveling speed of the vehicle 70. The vehicle 70 may be found by using a monitoring camera 45 installed on a street. Alternatively, the vehicle 70 may be found using position information obtained from an in-vehicle device of the vehicle 70. The notification unit 23 determines that the in-vehicle device of the vehicle 70 and a traffic signal 75 in the vicinity of the affected area a20 are output units 15.

The notification unit 23 transmits an attention request for the attention-requiring person P1 to the found output units 15. The traffic signal 75 in the vicinity of the affected area a20, when determined as the output unit 15, may be operated to stop the vehicle 70.

In the above embodiment, the notification unit 23 of the assistance system 20 executes the process for outputting a message (step S1-4). The notification unit 23 may change an output message based on the situation of the surrounding of where the attention-requiring person P1 is located. The assistance system 20 accesses an information server that transmits various types of information. The assistance system 20 includes an information storage unit that stores messages output in accordance with situations.

The assistance system 20 accesses the information server and obtains state information (surrounding situation) of an area where the attention-requiring person P1 is located. The state information may include event information, congestion information, disaster information, and accident information of the present area or neighboring areas. The assistance system 20 determines a message output based on the state information. This allows the assistance system 20 to positively issue an attention request to the output unit 15 in case of, for example, a disaster or congestion.

In the above embodiment, the area determining unit 22 of the assistance system 20 executes the process for determining an affected area (step S1-2). The affected area is predicted based on the flow line of the attention-requiring person P1. However, the method for determining the affected area is not limited to the use of a predicted flow line. The flow line may be determined using information input by, for example, the attention-requiring person P1. The assistance system 20 obtains a destination input to a mobile terminal or the like of the attention-requiring person P1 and uses an operation schedule to determine a movable body (such as train or bus) that may be used by the attention-requiring person P1 to reach the destination. The assistance system 20 may change an affected area and a message output by an output unit in the affected area depending on whether the attention-requiring person P1 will or will not ride the movable body. The assistance system 20 may also find a location where the attention-requiring person P1 should get off the movable body (e.g., train station or bus stop) in accordance with his or her destination. Further, depending on whether a stop is where the attention-requiring person will get off the movable body, the assistance system 20 may change the affected area or change the message output to an output unit in the affected area.

The assistance system 20 may predict a flow line based on the movement history of each attention-requiring person P1. In this case, the information storage unit of the assistance system 20 stores the movement history of each attention-requiring person P1. When detecting an attention-requiring person, the assistance system 20 may determine each attention-requiring person P1 and predict a routine flow line based on the movement history of the attention-requiring person P1.

Intersecting information that indicates the intersecting of the flow line of the attention-requiring person P1 with the flow line of a nearby object may be stored so that an affected area is predicted through machine learning.

In the above embodiment, the assistance system 20 includes the location determining unit 21, the area determining unit 22, and the notification unit 23. However, the assistance system 20 is not limited to such an integrated hardware structure. Functional units may be divided into plural devices.

The invention claimed is:

1. An assistance system comprising circuitry configured to:
   automatically determine a location of an attention-requiring person via detection by a monitoring camera installed in a facility and/or a global positioning system of a mobile terminal carried by the attention-requiring person;

determine, via the monitoring camera and/or the global positioning system, a movement of the attention-requiring person;

predict, via an area determining unit comprising a processor, a flow line of the attention-requiring person based on the location and a movement direction of the attention-requiring person as determined by the monitoring camera and/or the global positioning system, and based on a movement history of the attention-requiring person, the movement history of the attention-requiring person being stored in an information storage unit;

determine, via the area determining unit, an affected area based on the predicted flow line of the attention-requiring person;

automatically, via a notification unit, output via the mobile terminal an attention request to an output unit comprising a display that is present in the affected area; and automatically identify, via the notification unit, a motorized automobile that will intersect the affected area, wherein the affected area includes a region extending from the location of the attention-requiring person and, the output unit being in a fixed location near the affected area and comprising a traffic signal, and the display of the traffic signal changes to stop the motorized automobile in response to the request to prevent intersection and/or overlap of a flow line of the motorized automobile with the affected area.

2. The assistance system according to claim 1, wherein the assistance system is configured to find a nearby object that is included in the affected area as the attention-requiring person moves.

3. The assistance system according to claim 1, wherein the assistance system is configured to find the motorized automobile that is approaching so as to be included in the affected area.

4. The assistance system according to claim 1, wherein the assistance system is connected to the monitoring camera and the output unit via a network.

5. A method for assisting cooperation for a user that requires attention using an assistance system, the method comprising:
   automatically determining a location of an attention-requiring person via detection by a monitoring camera installed in a facility and/or a global positioning system of a mobile terminal carried by the attention-requiring person;
   determining, via the monitoring camera and/or the global positioning system, a movement of the attention-requiring person;
   predicting, via an area determining unit comprising a processor, a flow line of the attention-requiring person based on the location and a movement direction of the attention-requiring person as determined by the monitoring camera and/or the global positioning system, and based on a movement history of the attention-requiring person, the movement history of the attention-requiring person being stored in an information storage unit;
   determining, by the area determining unit, an affected area based on the predicted flow line of the attention-requiring person;
   automatically outputting, by the mobile terminal carried by the attention-requiring person, an attention request to an output unit comprising a display that is present in the affected area; and
   automatically identifying, via a notification unit, a motorized automobile that will intersect the affected area,
   wherein the affected area includes a region extending from the location of the attention-requiring person, and the output unit being in a fixed location near the affected area and comprising a traffic signal, and the display of the traffic signal changes to stop the motorized automobile in response to the request to prevent intersection and/or overlap of a flow line of the motorized automobile with the affected area.

6. The method according to claim 5, wherein the output unit is further identified by a communication device located in the facility, the communication device communicating with the output unit via a peer-to-peer network.

* * * * *